US010023509B2

(12) United States Patent
Pednekar et al.

(10) Patent No.: US 10,023,509 B2
(45) Date of Patent: Jul. 17, 2018

(54) PROCESSES AND APPARATUSES FOR PRODUCTION OF AROMATIC PRODUCTS

(71) Applicant: UOP LLC, Des Plaines, IL (US)

(72) Inventors: Abhishek M. Pednekar, Schaumburg, IL (US); Gregory R. Werba, Arlington Heights, IL (US); Saadet Ulas Acikgoz, Des Plaines, IL (US); Jason T. Corradi, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/687,193

(22) Filed: Aug. 25, 2017

(65) Prior Publication Data

US 2018/0093932 A1    Apr. 5, 2018

Related U.S. Application Data

(60) Provisional application No. 62/402,205, filed on Sep. 30, 2016.

(51) Int. Cl.
*C07C 5/27* (2006.01)
*B01J 19/24* (2006.01)
(Continued)

(52) U.S. Cl.
CPC .............. *C07C 5/277* (2013.01); *B01D 3/141* (2013.01); *B01D 3/40* (2013.01); *B01D 15/1821* (2013.01); *B01J 19/24* (2013.01); *B01J 2219/24* (2013.01)

(58) Field of Classification Search
CPC ... C07C 5/41; C07C 6/126; C10G 2300/1096; C10G 2300/202; C10G 2400/30;
(Continued)

(56) References Cited

U.S. PATENT DOCUMENTS 6,740,788 B1    5/2004   Maher et al.
7,371,912 B2    5/2008   Schultz et al.
(Continued)

OTHER PUBLICATIONS

Search Report dated Dec. 28, 2017 for corresponding PCT Appl. No. PCT/US2017/052445.

*Primary Examiner* — Sharon Pregler (57) ABSTRACT

Processes and apparatuses for producing a $C_8$ aromatic isomer product are provided. The apparatus comprises an isomerization unit to provide an isomerized stream. An isomerate stripper column is in communication with the isomerization unit to provide an isomerate stripper overhead stream comprising $C_{6-}$ hydrocarbons in an isomerate overhead line and an isomerate stripper bottoms stream in an isomerate bottoms line. A dividing wall naphthene splitter column is in communication with the isomerate bottoms line to provide an overhead naphthene splitter stream comprising the $C_8$ naphthenes and $C_7$ aromatic hydrocarbons in a naphthene splitter overhead line and a naphthene splitter sidedraw stream comprising $C_8$ aromatic isomers in a naphthene splitter sidedraw line. An extractive distillation column is in communication with the naphthene splitter overhead line to provide a recycle feedstream comprising the $C_8$ naphthenes in a recycle line and an extract stream comprising the $C_7$ aromatic hydrocarbons in an extract line.

20 Claims, 2 Drawing Sheets

(51) Int. Cl.
*B01D 3/40* (2006.01)
*B01D 3/14* (2006.01)
*B01D 15/18* (2006.01)

(58) Field of Classification Search
CPC ...... C10G 29/205; C10G 45/06; C10G 45/08; C10G 45/10; C10G 45/12; C10G 45/60; C10G 45/62; C10G 45/64
See application file for complete search history.

(56) References Cited

U.S. PATENT DOCUMENTS

| | | |
|---|---|---|
| 8,877,014 B2 | 11/2014 | Corradi et al. |
| 9,150,467 B2 * | 10/2015 | Noe .......................... C07C 5/41 |
| 9,302,953 B2 | 4/2016 | Molinier et al. |
| 9,309,169 B2 | 4/2016 | Ou John et al. |
| 2014/0179975 A1 | 6/2014 | Banerjee et al. |
| 2015/0038755 A1 | 2/2015 | Corradi et al. |
| 2016/0046544 A1 | 2/2016 | Molinier et al. |

* cited by examiner

PROCESSES AND APPARATUSES FOR PRODUCTION OF AROMATIC PRODUCTS

CROSS-REFERENCE TO RELATED APPLICATION

This application claims priority from Provisional Application No. 62/402,205 filed Sep. 30, 2016, the contents of which cited application are hereby incorporated by reference in its entirety.

TECHNICAL FIELD

The technical field generally relates to apparatuses and processes for producing a $C_8$ aromatic isomer product in an aromatics complex with an integrated scheme for handling naphthenes produced in the process. More particularly, the technical field relates to the apparatus and processes for reducing contaminants to a para-xylene separation unit in an aromatics complex producing para-xylene having an integrated scheme for handling naphthenes produced in the process.

BACKGROUND

Most new aromatics complexes are designed to maximize the yield of benzene and $C_8$ aromatic isomer (para-xylene, meta-xylene, ethylbenzene and ortho-xylene). Benzene is a versatile petrochemical building block used in many different products based on its derivation including ethylbenzene, cumene, and cyclohexane. In many instances, the sought $C_8$ aromatic isomer is para-xylene as para-xylene is an important building block, which is used almost exclusively for the production of polyester fibers, resins, and films formed via terephthalic acid or dimethyl terephthalate intermediates. Accordingly, an aromatics complex may be configured in many different ways depending on the desired products, available feedstocks, and investment capital available. A wide range of options permits flexibility in varying the product slate balance of benzene and para-xylene to meet downstream processing requirements.

A prior art aromatics complex flow scheme has been disclosed by Meyers in the HANDBOOK OF PETROLEUM REFINING PROCESSES, 2d. Edition in 1997 by McGraw-Hill.

In an aromatics complex, the production of commercial-grade $C_8$ aromatic isomers involves multiple separation steps such as fractionation, adsorptive separation and/or crystallization and reaction steps including transalkylation, isomerization, dealkylation etc. In typical aromatic complexes used to produce high purity $C_8$ aromatic isomers, the isomer-depleted raffinate stream from the separation process, either simulated moving bed adsorption or crystallization, is sent to an isomerization process in which the remaining xylene isomers are isomerized to produce the desired isomer (near equilibrium concentration) and convert ethylbenzene (EB) to other components which can be separated via fractionation or other means. One type of xylene isomerization process also isomerizes EB to xylenes via a $C_8$ naphthene intermediate. In a typical paraxylene complex using simulated moving bed (SMB) adsorption, the $C_8$ naphthenes remain in the feed to the SMB unit. This is feasible due to the typical use of para-diethylbenzene as the desorbent in the SMB process. In paraxylene complexes using toluene as the SMB desorbent, the majority of the $C_8$ napthenes must be removed from the feed to the SMB unit in order to avoid accumulation of the $C_8$ naphthenes in the circulating toluene desorbent. This also holds true for complexes designed to produce meta-xylene which also utilizes toluene as the SMB desorbent. This is necessary because the $C_8$ naphthene isomers have boiling points within the range of toluene (at the low end) and xylenes (at the high end). As a result, $C_8$ isomers, such as 1,1,3-trimethyl cyclopentane which has a boiling point slightly lower than toluene, will accumulate in the toluene desorbent supply, thus making the material less suitable as a desorbent. In addition, because some of the $C_8$ naphthene isomers have boiling points close to toluene and toluene is a byproduct produced in the xylene/EB isomerization process, it is also necessary to remove toluene from the $C_8$ naphthene recycle stream to avoid accumulation of toluene in the isomerization feed.

Further, the feed stream separated from $C_8$ naphthenes which is passed to the xylene separation unit may contain higher molecular weight hydrocarbons i.e. $C_{9+}$ components as contaminants making the xylene separation process inefficient.

Accordingly, it is desirable to provide improved methods and apparatuses for separating $C_8$ naphthenes from an isomerate product stream before being recycled to the xylene separation unit. Further, it is desirable to provide a cost-effective method and apparatus to solve the problem of accumulation of $C_8$ naphthenes in the desorbent supply in a xylene separation unit. Also, it is desirable to remove toluene from the $C_8$ naphthene recycle stream to avoid accumulation of toluene in the isomerization feed. Moreover, it is desirable to reduce the amount of $C_{9+}$ alkylaromatic hydrocarbons being passed to the xylene separation unit as contaminants in an efficient and cost-effective way. Furthermore, other desirable features and characteristics of the present subject matter will become apparent from the subsequent detailed description of the subject matter and the appended claims, taken in conjunction with the accompanying drawings and this background of the subject matter.

BRIEF SUMMARY

Various embodiments contemplated herein relate to apparatuses and processes for producing a purified $C_8$ aromatic isomer product in an aromatics complex. The exemplary embodiments taught herein include apparatuses and processes for reducing contaminants comprising $C_{9+}$ hydrocarbons to a para-xylene separation unit in an aromatics complex producing para-xylene and having an integrated scheme for handling naphthenes produced in the process.

In accordance with an exemplary embodiment, an apparatus is provided for producing para-xylene, wherein the apparatus comprises an isomerization unit to provide an isomerized stream. An isomerate stripper column is in communication with the isomerization unit to provide an isomerate stripper overhead stream comprising $C_{6-}$ hydrocarbons in an isomerate overhead line and an isomerate stripper bottoms stream in an isomerate bottoms line. A dividing wall naphthene splitter column is in communication with the isomerate bottoms line to provide an overhead naphthene splitter stream comprising the $C_8$ naphthenes and $C_7$ aromatic hydrocarbons in a naphthene splitter overhead line and a naphthene splitter sidedraw stream comprising $C_8$ aromatic isomers in a naphthene splitter sidedraw line. An extractive distillation column is in communication with the naphthene splitter overhead line to provide a recycle feedstream comprising the $C_8$ naphthenes in a recycle line and an extract stream comprising the $C_7$ aromatic hydrocarbons in an extract line.

In accordance with another exemplary embodiment, an apparatus is provided for producing para-xylene, wherein the apparatus comprises an isomerization unit to provide an isomerized stream. An isomerate stripper column is in communication with the isomerization unit to provide an isomerate stripper overhead stream comprising $C_{6-}$ hydrocarbons in an isomerate overhead line and an isomerate stripper bottoms stream in an isomerate bottoms line. A dividing wall naphthene splitter column is in communication with the isomerate bottoms line to provide an overhead naphthene splitter stream comprising the $C_8$ naphthenes and $C_7$ aromatic hydrocarbons in a naphthene splitter overhead line and a naphthene splitter sidedraw stream comprising $C_8$ aromatic isomers in a naphthene splitter sidedraw line. The dividing wall column having one or more vapor-liquid contacting stages comprising a dividing wall having an upper end and a lower end that divides the naphthene splitter column into a feed section and a product section and the lower end of the dividing wall extends to a last stage of the one or more vapor-liquid contacting stages. An extractive distillation column is in communication with the naphthene splitter overhead line to provide a recycle feedstream comprising the $C_8$ naphthenes in a recycle line and an extract stream comprising the $C_7$ aromatic hydrocarbons in an extract line.

In accordance with another exemplary embodiment, a process is provided for the production of para-xylene, wherein the process comprises introducing a raffinate product stream comprising $C_8$ aromatic isomers to an isomerization unit to provide an isomerized stream, wherein the isomerized stream is produced in the presence of an ethylbenzene (EB) isomerization catalyst. The isomerized stream is passed to an isomerate stripper column to provide an isomerate stripper overhead stream comprising $C_{6-}$ hydrocarbons and an isomerate stripper bottoms stream. The isomerate stripper bottoms stream is passed to a dividing wall naphthene splitter column to provide an overhead naphthene splitter stream comprising the $C_8$ naphthenes and $C_7$ aromatic hydrocarbons and a naphthene splitter sidedraw stream comprising $C_8$ aromatic isomers and less than about 1 wt % of $C_{9+}$ alkylaromatic hydrocarbons. The overhead naphthene splitter stream is passed to an extractive distillation column to provide a recycle feedstream comprising the $C_8$ naphthenes and an extract stream comprising the $C_7$ aromatic hydrocarbons. Finally, the recycle feedstream is passed to the isomerization unit.

These and other features, aspects, and advantages of the present disclosure will become better understood upon consideration of the following detailed description, drawings and appended claims.

BRIEF DESCRIPTION OF THE DRAWINGS

The various embodiments will hereinafter be described in conjunction with the following FIGURES, wherein like numerals denote like elements.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DEFINITIONS

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

As used herein, the term "overhead stream" can mean a stream withdrawn at or near a top of a vessel, such as a column.

As used herein, the term "bottoms stream" can mean a stream withdrawn at or near a bottom of a vessel, such as a column.

Hydrocarbon molecules may be abbreviated $C_1$, $C_2$, $C_3$, $C_n$ where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, $A_n$ where "n" represents the number of carbon atoms in the one or more aromatic molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "zone" or "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top or overhead pressure is the pressure of the overhead vapor at the vapor outlet of the column. The bottom temperature is the liquid bottom outlet temperature. Overhead lines and bottoms lines refer to the net lines from the column downstream of any reflux or reboil to the column unless otherwise shown. Stripping columns omit a reboiler at a bottom of the column and instead provide heating requirements and separation impetus from a fluidized inert media such as steam.

As used herein, the term "rich" can mean an amount of at least generally 50%, and preferably 70%, by mole, of a compound or class of compounds in a stream.

As depicted, process flow lines in the FIGURES can be referred to interchangeably as, e.g., lines, pipes, feeds, gases, products, discharges, parts, portions, or streams.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "predominantly" means a majority, suitably at least 50 mol % and preferably at least 60 mol %.

The term "passing" means that the material passes from a conduit or vessel to an object.

The term "majority" means, suitably at least 40 wt % and preferably at least 50 wt %

DETAILED DESCRIPTION

The following detailed description is merely exemplary in nature and is not intended to limit the various embodiments or the application and uses thereof. Furthermore, there is no intention to be bound by any theory presented in the preceding background or the following detailed description. Moreover, the reaction conditions including selection of temperature, pressure, LHSV and catalyst in the various units in the aromatics complex described below are conventional which are known to one of ordinary skill in the art, unless wherever mentioned.

Figure 1:
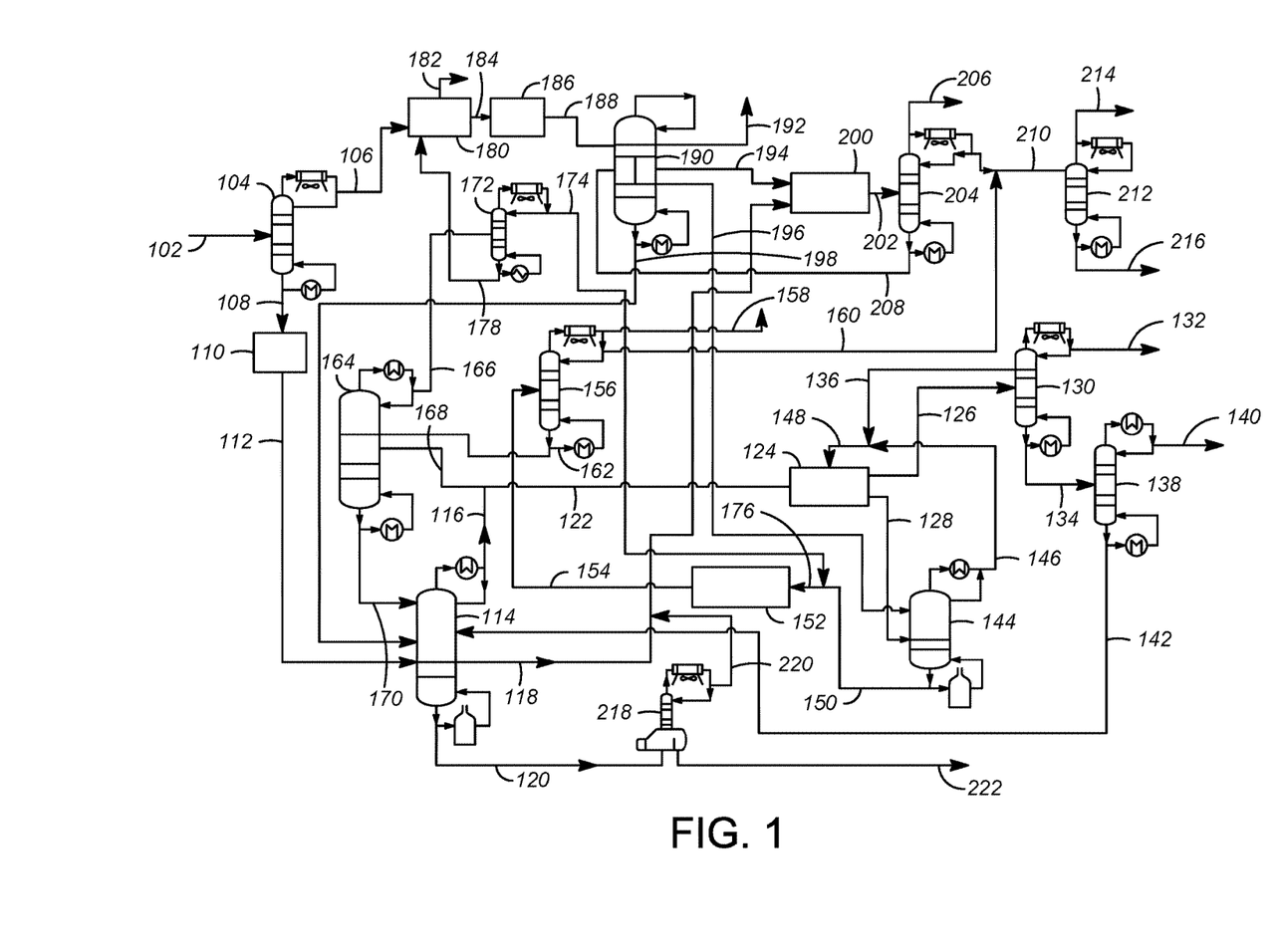
FIG. 1 illustrates an aromatics complex having an integrated scheme for handling naphthenes produced in the process according to an embodiment of the present disclosure.

An exemplary embodiment of the process and apparatus for reducing contaminants comprising $C_{9+}$ hydrocarbons to a para-xylene separation unit in an aromatics complex producing $C_8$ aromatic isomer product with an integrated scheme for handling naphthenes produced in the process is addressed with reference to a process and apparatus 100 as shown in FIG. 1. The process and apparatus 100 includes a reformate splitter column 104, an aromatics rerun column 114, a xylene separation unit 124, an extract column 130, a xylene column 138, a raffinate column 144, an isomerization unit 152, an isomerate stripper column 156, a dividing wall naphthene splitter column 164, an extractive distillation column 172, an aromatics extraction unit 180, a benzene-toluene (BT) column 188, a transalkylation unit 200, a transalkylation stripper 204, a stabilizer 212 and a heavy aromatics column 218.

In accordance with an exemplary embodiment as shown in FIG. 1, a reformate stream in line 102 comprising aromatic hydrocarbons may be passed to the reformate splitter column 104. A reformate overhead stream in line 106 comprising $C_{7-}$ aromatic hydrocarbons and a reformate bottoms stream in line 108 comprising $C_{7+}$ aromatic hydrocarbons may be withdrawn from the reformate splitter column 104. In accordance with an instant embodiment as shown, an overhead stream from the reformate splitter column 106 may be condensed and separated in a receiver with a portion of the condensed liquid being refluxed back to the reformate splitter column 104 to obtain the reformate overhead stream from a net portion in line 106. Further, as illustrated, the reformate splitter column 104 may include a reboiler at a bottom of the column to vaporize and send a portion of the reformate bottoms stream back to the bottom of the column. The reformate bottoms stream in line 108 may be passed to the aromatics rerun column 114 for separation. In accordance with an exemplary embodiment as shown in FIG. 1, the reformate bottoms stream in line 108 may be passed through a clay treater 110 to treat residual olefin contaminants and provide a treated reformate bottoms stream in line 112 prior to being passed to the aromatics rerun column 114. The aromatics rerun column 114 may further receive a naphthene splitter bottoms stream in line 170 comprising $C_{8+}$ aromatic hydrocarbons and a benzene toluene (hereinafter "BT") column bottoms stream in line 198 comprising xylenes. Further, the aromatics rerun column 114 may receive $C_{8+}$ aromatic hydrocarbons in a bottoms stream in line 142 from the xylene column 138 discussed later. A net overhead rerun column stream in line 116 comprising $C_8$ aromatic isomers and a net bottoms rerun column stream in line 120 rich in $C_9$ and heavier alkylaromatic hydrocarbons may be withdrawn from the aromatics rerun column 114.

In accordance with an exemplary embodiment as shown, the net overhead rerun column stream may be recovered from an overhead of the aromatics rerun column 114 after condensing, flashing and refluxing a portion of the overhead stream from the column. Further, as illustrated, the aromatics rerun column 114 may include a heater at a bottom of the column to vaporize and send a portion of the bottoms stream back to the bottom of the column. A rerun column sidedraw stream in line 118 rich in $C_9$ and $C_{10}$ alkylaromatics may also be withdrawn from the aromatic rerun column 114. In accordance with an exemplary embodiment as shown in FIG. 1, the rerun column sidedraw stream in line 118 may be passed to the transalkylation unit 200.

In accordance with an exemplary embodiment as shown in FIG. 1, the net overhead rerun column stream in line 116 may be combined with a naphthene splitter sidedraw stream in line 168 comprising $C_8$ aromatic isomers to provide a mixed stream in line 122. The mixed stream in line 122 includes para-xylene, meta-xylene, ortho-xylene and ethylbenzene and may be subsequently passed to the xylene separation unit 124 to obtain a desired $C_8$ aromatic isomer product via a separation process. The xylene separation unit 124 may be one of a para-xylene separation unit, a meta-xylene separation unit or an ortho-xylene separation unit depending on the $C_8$ aromatic product desired and the operating conditions can be tailored accordingly. In accordance with an exemplary embodiment as discussed, the xylene separation unit 124 is a para-xylene separation unit and will be referred to as the para-xylene separation unit 124 for the purpose of the discussion of the instant embodiment. In accordance with the instant embodiment as discussed, the separation process operates, preferably via simulated moving adsorption bed (SMB) employing a desorbent, to provide a xylene extract stream in line 126 which is para-xylene extract stream comprising a mixture of para-xylene and desorbent for the instant embodiment. Examples of desorbent include, and are not limited to toluene and para-diethylbenzene. In accordance with the instant embodiment, toluene is used as the desorbent. The para-xylene extract stream in line 126 may be passed to the extract column 130 which separates para-xylene from the desorbent. A para-xylene stream in line 134 may be withdrawn comprising the desired para-xylenes from the extract column 130. Further, a first return desorbent stream in line 136 is withdrawn which may be subsequently recycled to the para-xylene separation unit 124. In an aspect as shown in FIG. 1, a desorbent drag stream in line 132 may also be withdrawn from the extract column 130. In accordance with an exemplary embodiment, the desorbent drag stream in line 132 may comprise primarily $C_{7-}$ hydrocarbons and may be passed to the BT column 190. In accordance with another exemplary embodiment, the desorbent drag stream in line 132 may be passed to the extractive distillation column 172 to recover additional $C_8$ naphthenes. The para-xylene stream in line 134 may be passed to the para-xylene column to separate the para-xylene product in line 140 from the heavier hydrocarbons obtained as a bottoms stream in line 142 which may be subsequently recycled to the aromatics rerun column 114.

A raffinate stream in line 128 comprising non-equilibrium mixture of $C_8$ aromatics raffinate and the desorbent may be also withdrawn from the para-xylene separation unit 124. The raffinate stream in line 128 may be passed to the raffinate column 144. In accordance with an exemplary embodiment as shown in FIG. 1, a second toluene-enriched stream in line 196 from the BT column 190 may also be introduced to the raffinate column 144 which may act as a makeup for the toluene being used as the desorbent in the para-xylene separation process as per the instant embodiment. The raffinate column 144 separates a raffinate product stream in line 150 for isomerization in isomerization unit 152 from a second return desorbent stream in line 146. In accordance with an exemplary embodiment as shown in FIG. 1, the first desorbent rerun in line 136 and the second desorbent rerun stream in line 146 may combine to provide a combined desorbent rerun stream in line 148 which may be subsequently passed to the para-xylene separation unit 124.

The raffinate product stream in line 150 comprising a non-equilibrium mixture of xylene isomers and ethylbenzene is introduced to the isomerization unit 152 to provide an isomerized stream in line 154. In accordance with an exemplary embodiment as shown in FIG. 1, a recycle feedstream in line 174 (discussed later) from the extractive distillation column 172 may be recycled to the isomerization unit 152. As shown, the recycle stream in line 174 may combine with the raffinate product stream in line 150 to provide a combined stream in line 176 which may be subsequently passed to the isomerization unit 152. The raffinate product stream is isomerized in reactor 152, which contains an isomerization catalyst to provide a product approaching equilibrium concentrations of $C_8$ aromatic isomers. In accordance with the instant embodiment as discussed for producing para-xylenes, additional para-xylene may be produced by reestablishing an equilibrium or near-equilibrium distribution of xylene isomers. Isomerization catalysts that can be used in the present disclosure include conventional isomerization catalysts such as those disclosed in U.S. Pat. No. 6,740,788, the teachings of which are incorporated herein by reference. In accordance with an exemplary embodiment as discussed, the isomerization catalyst is an ethylbenzene (hereinafter "EB") isomerization catalyst. An isomerized stream is withdrawn in line 154 from the isomerization unit 152. In the instant aspect as discussed using an ethylbenzene EB isomerization catalyst, the conversion of ethylbenzene to additional xylenes takes place via a $C_8$ naphthene intermediate. Also, toluene may be produced as a byproduct in the isomerization process. Accordingly, the isomerized stream 154 may include $C_8$ naphthenes and toluene.

Figure 2:
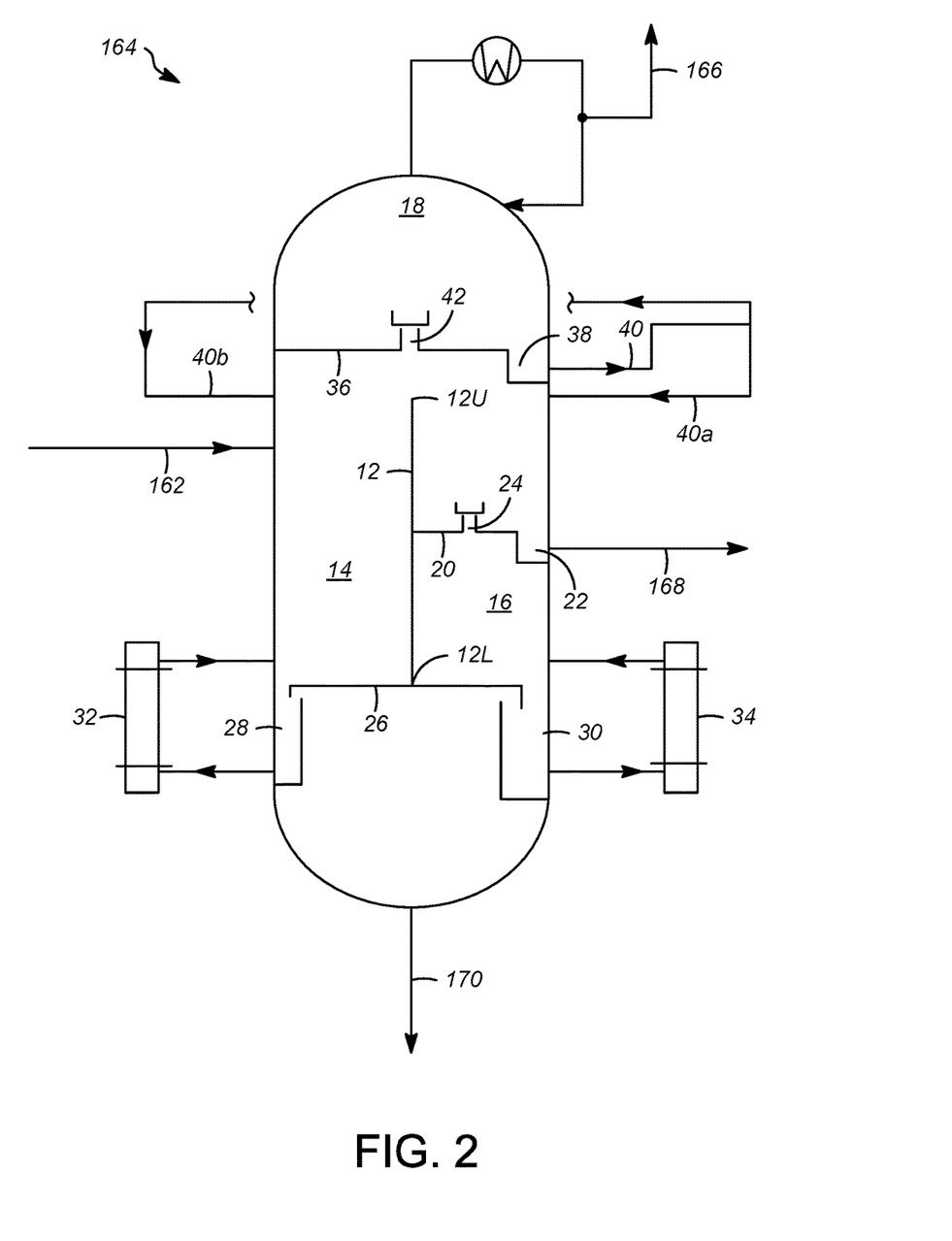
FIG. 2 illustrates a dividing wall naphthene splitter column according to an embodiment of the present disclosure.

The isomerized stream in line 154 may be passed to the isomerate stripper column 156 to separate an isomerate stripper overhead stream comprising $C_{6-}$ hydrocarbons in an isomerate overhead line 160 from an isomerate stripper bottoms stream comprising the $C_8$ naphthenes and toluene in isomerate bottoms line 162, at a first pressure. A vaporous stream in line 158 comprising lighter ends may also be withdrawn from the isomerate stripper column 156 and passed to a vent gas compressor and a stabilizer condenser. The isomerate stripper bottoms stream in isomerate bottoms line 162 may be passed to the dividing wall naphthene splitter column 164 for further separation. Accordingly, the dividing wall naphthene splitter column 164 may be in communication with the isomerate bottoms line 162. In an aspect, the dividing wall naphthene splitter column 164 is in direct, downstream communication with the isomerate bottoms line 162. Referring now to FIG. 2 illustrating the dividing wall naphthene splitter column 164 according to a representative embodiment of the invention. As illustrated, a vertically elongated dividing wall 12, located substantially centrally in the interior of the column 164, separates a significant portion of the column interior, along the column height, into a feed section 14 and a product section 16. For simplicity, conventional vapor-liquid contacting devices such as trays or packing materials are not shown, although these contacting devices are present throughout feed and product sections 14, 16, where they extend across only a portion of the column diameter in these respective sections. Such contacting devices are also generally present in a common upper section 18 which may be positioned above dividing wall 12. Accordingly, the dividing wall naphthene splitter column 164 includes o or more vapor-liquid contacting stages and includes the dividing wall 12 having an upper end 12U and a lower end 12L that divides the naphthene splitter column into the feed section 14 and the product section 16. In accordance with an exemplary embodiment as shown in FIG. 2, the lower end 12L of the dividing wall 12 extends to a last stage of the one or more vapor-liquid contacting stages. As shown in FIG. 2, the feed section 14 of the dividing wall naphthene splitter column may be in communication with the isomerate bottoms line 162.

An overhead naphthene splitter stream in line 166 comprising the $C_8$ naphthenes and toluene is separated from the naphthene splitter bottoms stream in line 170 comprising $C_{8+}$ aromatic hydrocarbons in the dividing wall naphthene splitter column 164, at a second pressure. In accordance with an exemplary pressure, the second pressure is greater than the first pressure. Accordingly, in an aspect, the dividing naphthene splitter column 164 operates at a higher pressure than the isomerate stripper column 156. Further, the naphthene splitter sidedraw stream in line 168 comprising $C_8$ aromatic isomers is also withdrawn which may be subsequently passed to the para-xylene separation unit 124 for further processing as discussed above. In various embodiments, the overhead naphthene splitter stream in line 166, the naphthene splitter sidedraw stream in line 168 and the naphthene splitter bottoms stream in line 170 may be in downstream communication with the product section 16 of the dividing wall naphthene splitter column 164. In accordance with various embodiments, the overhead naphthene splitter stream in line 166 comprises a majority of the $C_8$ naphthenes present in the isomerized stream and the naphthene splitter sidedraw stream in line 168 comprises majority of the $C_8$ aromatic isomers present in the isomerized stream. Additionally, the naphthene splitter sidedraw stream in line 168 comprises heavier hydrocarbon compounds such as $C_{9+}$ alkylaromatic hydrocarbons which may slip into the naphthene splitter sidedraw stream as contaminants. In conventional columns, a naphthene splitter sidedraw stream may comprise about 2 wt % of $C_{9+}$ alkylaromatic hydrocarbons. However, applicants have found that using the dividing wall naphthene splitter column as described in the present disclosure, the amount of $C_{9+}$ hydrocarbons slipping into the naphthene splitter sidedraw streams are significantly reduced. In accordance with an exemplary embodiment according to the present disclosure, the naphthene splitter sidedraw stream in line 168 may comprise less than about 1 wt % of $C_{9+}$ alkylaromatic hydrocarbons. In another aspect, the naphthene splitter sidedraw stream in line 168 may comprise less than about 0.7 wt % of $C_{9+}$ alkylaromatic hydrocarbons. In yet another aspect, the naphthene splitter sidedraw stream in line 168 may comprises between about 0.5 wt % to about 1 wt % of $C_{9+}$ alkylaromatic hydrocarbons. Applicants have found that the risk of heavy boiling components slipping into the naphthene splitter sidedraw stream is reduced due to the location of the side draw in the divided wall column as compared to a conventional side draw column. As shown, the feed is on the pre fractionation side i.e. the feed section 14 of the dividing wall 12 and the side draw is on the product side i.e. the product section 16, thereby inherently mitigating the risk of contamination of the feed to para-xylene unit.

In various embodiments, the para-xylene separation unit 124 may be in downstream communication with the product section 16 of the dividing wall naphthene splitter column via the naphthene splitter sidedraw line 168. The column is designed and operated such that the liquid flowing downward through the product section of the column is intercepted by a substantially imperforate tray 20 extending across a midsection of the product section 16 of the column in an exemplary vapor-liquid contacting stage. The tray 20 has a liquid collection well 22 in which a quantity of this descending liquid is collected. The level of the liquid in this well may be monitored by a controller not illustrated. A stream of the collected liquid is withdrawn from the liquid collection well 22 as the naphthene splitter sidedraw stream in line 168. The trap out tray located in a central region of the product section of the dividing wall naphthene splitter column also contains a vapor chimney 24 to allow the upward passage of vapor through the product section. An overflow weir may also be provided on this trap out tray, with this weir allowing liquid in excess of that required for the generation of the side product stream of line 168 to overflow the weir and to continue downward to the remainder of the product section.

Further, bottom half of the column shows another exemplary vapor-liquid contacting stage comprising a tray 26. In accordance with an exemplary embodiment as shown in FIG. 2, the vapor-liquid contacting stage comprising the tray 26 is the last vapor-liquid contacting stage of the dividing wall naphthene splitter column 164. Accordingly, no stage exists below this stage. Further, as shown, the lower end 12L of the dividing wall 12 extends to tray 26 of the last vapor-liquid contacting stage. The instant vapor-liquid contacting stage further includes two liquid collection wells 28 and 30 in which the descending liquid is collected. A portion of this descending liquid may be withdrawn as the naphthene splitter bottoms stream in line 170. Further, one or more reboilers comprising a first reboiler 32 and a second reboiler 34 are in communication with the liquid collection wells 28 and 30 respectively, to vaporize and send a portion of a bottoms stream back to the bottom of the column. In accordance with an exemplary embodiment, vapor coming from each of the reboiler 32 and 34 is controlled using a vapor control mechanism so that the vapor is evenly distributed close to the amount needed for the overall column. Accordingly, constant vapor fractions are provided to each side of the dividing wall naphthene splitter column 164.

Another exemplary vapor-liquid contacting stage is shown in the upper half of the column comprising a tray 36. The tray 36 has a liquid collection well 38 in which a quantity of the descending liquid is collected. The level of the liquid in this well may be monitored by a controller not illustrated. A stream of the collected liquid is withdrawn from the liquid collection well 38 in line 40. As shown in FIG. 2, liquid conduits 40a, 40b are used to provide liquid flow from liquid collection well 38 to both feed and product sections 14, 16 on opposite sides of dividing wall 12. Both liquid conduits 40a, 40b, which provide fluid communication to feed and product sections 14, 16, are shown in FIG. 1 as being external to the column and thereby readily controlled using control valves and flow measurement systems (not shown). Material in liquid conduits, 40a and/or 40b, may be conveyed to feed and product sections 14, 16 using pumps (not shown) or otherwise via gravity in the case of a free draining system. The trays in the dividing wall naphthene splitter column 164 are high performance trays. The high performance trays can accommodate more vapor and liquid than conventional trays. Suitable high performance trays include, but are not limited to, UOP MD™ trays.

Referring back to FIG. 1, the overhead naphthene splitter stream in line 166 may be passed to the extractive distillation column 172. Accordingly, the extractive distillation column 172 may be in communication with the naphthene splitter overhead line 166. In an aspect, the extractive distillation column 172 may be in direct, downstream communication with the naphthene splitter overhead line 166. In an aspect, the extractive distillation column 172 is in downstream communication with the naphthene splitter overhead line from the product section 16 of the dividing wall naphthene splitter column 164. Extractive distillation is a technique for separating mixtures of components having nearly equal volatility and having nearly the same boiling point. In extractive distillation, a solvent is introduced into a main extractive-distillation column above the entry point of the hydrocarbon-containing fluid mixture that is to be separated. The solvent affects the volatility of the hydrocarbon-containing fluid component boiling at a higher temperature differently than the hydrocarbon-containing fluid component boiling at a lower temperature sufficiently to facilitate the separation of the various hydrocarbon-containing fluid components by distillation and such solvent exits with the bottoms fraction. The extractive distillation process in extractive distillation column 172 takes place in the presence of a solvent and separates $C_8$ naphthenes in a recycle feedstream in the recycle line 174 from an extract stream comprising the $C_7$ aromatic hydrocarbons and the solvent withdrawn in an extract line 178. Suitable solvents include tetrahydrothiophene 1,1-dioxide (or sulfolane), NFM (n-formylmorpholine), NMP (n-methylpyrrolidone), diethylene glycol, triethylene glycol, tetraethylene glycol, methoxy triethylene glycol, and mixtures thereof. Other glycol ethers may also be suitable solvents alone or in combination with those listed above. The recycle feedstream in line 174 may be passed to the isomerization unit 152 and processed together with raffinate product stream in line 150 as discussed above. The extract stream in line 178 may be sent to a solvent-recovery column for the separation of the solvent from the $C_7$ aromatic hydrocarbons. In accordance with an exemplary embodiment as shown in FIG. 1, the extract stream is passed to the aromatics extraction unit 180.

Referring back to the reformate splitter column 104, the reformate overhead stream in line 106 comprising $C_{7-}$ aromatic hydrocarbons may be passed to the aromatics extraction unit 180. The aromatics extraction unit 180 can comprise different methods of separating aromatics from a hydrocarbon stream. One industry standard is the Sulfolane™ process, which is an extractive distillation process utilizing sulfolane to facilitate high purity extraction of aromatics. The Sulfolane™ process is well known to those skilled in the art. An aromatics extract stream in line 184 comprising benzene and toluene and a raffinate stream in line 182 comprising non-aromatic hydrocarbons may be withdrawn from the aromatics extraction unit 180. The aromatics extract stream in line 184 may be passed to the BT column 190 to provide benzene and toluene via separation. In accordance with an exemplary embodiment as shown in FIG. 1, the aromatics extract stream in line 184 may be passed through a clay treater 186 to treat residual olefin contaminants and provide a treated aromatics extract stream in line 188 prior to being passed to the BT column 190. A transalkylation bottom stream in line 208 from the transalkylation stripper column 204 may also be passed to the BT column 190. A benzene-enriched stream in line 192, a first toluene-enriched stream in line 194 and the second toluene-enriched stream in line 196 are withdrawn from the BT column 190. Further, the BT column bottoms stream in line 198 is withdrawn and sent to the aromatics rerun column 114 for further processing as discussed above. The second toluene-enriched stream in line 196 may be passed to the raffinate column 144 as also discussed above. The first toluene-enriched stream in line 194 may be passed to the transalkylation unit 200 for production of additional xylenes and benzene.

In accordance with an exemplary embodiment as shown in FIG. 1, in addition to first toluene-enriched stream, the aromatic rerun column sidedraw stream in line 118 rich in $C_9$ and $C_{10}$ alkylaromatics may be passed to the transalkylation unit 200 along with a heavy aromatics column overhead stream in line 220 rich in $C_9$ and $C_{10}$ alkylaromatics from the heavy aromatics column 218. In accordance with an exemplary embodiment as shown in FIG. 1, the aromatic rerun column sidedraw stream in line 118 and the heavy aromatics column overhead stream in line 220 combine to provide a mixed alkylaromatic feedstream in line 224, which may be subsequently provided to the transalkylation unit 200. A make-up hydrogen gas stream (not shown) may also be provided to the transalkylation unit 200. In the transalkylation unit 200, the incoming feedstreams may be contacted with a transalkylation catalyst under transalkylation conditions. In the transalkylation unit 200, the process continues by transalkylating $C_9$ and $C_{10}$ alkylaromatics with toluene. A transalkylated stream in line 202 comprising benzene and xylenes may be withdrawn from the transalkylation unit 200.

Transalkylation catalysts that can be used in the present disclosure include conventional transkylation catalysts such as those disclosed in U.S. Pat. No. 6,740,788, the teachings of which are incorporated herein by reference. Conditions employed in the transalkylation unit 200 normally include a temperature of from about 200° C. to about 540° C. The transalkylation unit 200 is operated at moderately elevated pressures broadly ranging from about 1 kg/cm' to about 60 kg/cm². The transalkylation reaction can be effected over a wide range of space velocities, with higher space velocities affecting a higher ratio of para-xylene at the expense of conversion. Liquid hourly space velocity generally is in the range of from about 0.1 to about 20 $hr^{-1}$.

The transalkylated stream in line 202 may be sent to transalkylation stripper 204 to recover the transalkylation stripper bottoms stream in line 208. Light ends may be removed in transalkylation stripper overhead stream in line 206 and a net overhead stream in line 210 comprising $C_6$ and lighter hydrocarbons may also be withdrawn from the transalkylation stripper 204. Subsequently, the transalkylation stripper bottoms stream in line 208 may be recycled to the BT column 190 to recover benzene product and unconverted toluene for further processing as previously described. The net overhead stream in line 210 may be passed to the stabilizer 212 to provide a stabilizer overhead vaporous stream in line 214 and a stabilizer bottoms stream in line 216. The stabilizer bottoms stream in line 216 may be passed to the aromatics extraction unit 180.

Referring back to the aromatic rerun column 114, net bottoms rerun column stream in line 120 rich in $C_9$ and heavier alkylaromatic hydrocarbons is passed to the heavy aromatics column 218 to separate heavy aromatics comprising $C_{11+}$ alkylaromatic hydrocarbons from $C_9$ and $C_{10}$ alkylaromatics recovered as the heavy aromatics column overhead stream in line 220. The $C_{11+}$ alkylaromatic hydrocarbons may be withdrawn from the heavy aromatics column 218 as a bottoms stream in line 222. The heavy aromatics column overhead stream in line 220 rich in $C_9$ and $C_{10}$ alkylaromatics may be passed to the transalkylation unit 200 for production of additional xylenes and benzene as previously described.

SPECIFIC EMBODIMENTS

While the following is described in conjunction with specific embodiments, it will be understood that this description is intended to illustrate and not limit the scope of the preceding description and the appended claims.

A first embodiment of the invention is an apparatus for producing para-xylene, wherein the apparatus comprises a) an isomerization unit to provide an isomerized stream; b) an isomerate stripper column in communication with the isomerization unit to provide an isomerate stripper overhead stream comprising $C_{6-}$ hydrocarbons in an isomerate overhead line and an isomerate stripper bottoms stream in an isomerate bottoms line; c) a dividing wall naphthene splitter column in communication with the isomerate bottoms line to provide an overhead naphthene splitter stream comprising the $C_8$ naphthenes and $C_7$ aromatic hydrocarbons in a naphthene splitter overhead line and a naphthene splitter sidedraw stream comprising $C_8$ aromatic isomers in a naphthene splitter sidedraw line; and d) an extractive distillation column in communication with the naphthene splitter overhead line to provide a recycle feedstream comprising the $C_8$ naphthenes in a recycle line and an extract stream comprising the $C_7$ aromatic hydrocarbons in an extract line. An embodiment of the invention is one, any or all of prior embodiments in this paragraph up through the first embodiment in this paragraph, wherein the dividing wall naphthene splitter column comprises a dividing wall having an upper end and a lower end that divides the naphthene splitter column into a feed section and a product section. An embodiment of the invention is one, any or all of prior embodiments in this paragraph up through the first embodiment in this paragraph, wherein the dividing wall naphthene splitter column comprises one or more vapor-liquid contacting stages. An embodiment of the invention is one, any or all of prior embodiments in this paragraph up through the first embodiment in this paragraph, wherein the lower end of the dividing wall extends to a last stage of the one or more vapor-liquid contacting stages. An embodiment of the invention is one, any or all of prior embodiments in this paragraph up through the first embodiment in this paragraph, wherein the feed section of the dividing wall naphthene splitter column is in downstream communication with the isomerate bottoms line. An embodiment of the invention is one, any or all of prior embodiments in this paragraph up through the first embodiment in this paragraph further comprising a para-xylene separation unit in downstream communication with the product section of the dividing wall naphthene splitter column via the naphthene splitter sidedraw line. An embodiment of the invention is one, any or all of prior embodiments in this paragraph up through the first embodiment in this paragraph, wherein the para-xylene separation unit being a simulated moving bed adsorption unit using toluene as a desorbent. An embodiment of the invention is one, any or all of prior embodiments in this paragraph up through the first embodiment in this paragraph, wherein the extractive distillation column in is downstream communication with the naphthene splitter overhead line from the product section of the dividing wall naphthene splitter column. An embodiment of the invention is one, any or all of prior embodiments in this paragraph up through the first embodiment in this paragraph further comprising an aromatics rerun column in downstream communication with a naphthene splitter bottoms line from the product section of the dividing wall naphthene splitter column.

A second embodiment of the invention is an apparatus for producing para-xylene, wherein the apparatus comprises a) an isomerization unit to provide an isomerized stream; b) an isomerate stripper column in communication with the isomerization unit to provide an isomerate stripper overhead stream comprising $C_{6-}$ hydrocarbons in an isomerate overhead line and an isomerate stripper bottoms stream in an isomerate bottoms line; c) a dividing wall naphthene splitter column having one or more vapor-liquid contacting stages comprising a dividing wall having an upper end and a lower end that divides the naphthene splitter column into a feed section and a product section and the lower end of the dividing wall extends to a last stage of the one or more vapor-liquid contacting stages, the dividing wall naphthene splitter being in communication with the isomerate bottoms line to provide an overhead naphthene splitter stream comprising the $C_8$ naphthenes and $C_7$ aromatic hydrocarbons in a naphthene splitter overhead line and a naphthene splitter sidedraw stream comprising $C_8$ aromatic isomers in a naphthene splitter sidedraw line; and d) an extractive distillation column in communication with the naphthene splitter overhead line to provide a recycle feedstream comprising the $C_8$ naphthenes in a recycle line and an extract stream comprising the $C_7$ aromatic hydrocarbons in an extract line. An embodiment of the invention is one, any or all of prior embodiments in this paragraph up through the second embodiment in this paragraph, wherein the feed section of the dividing wall naphthene splitter column is in communication with the isomerate bottoms line. An embodiment of the invention is one, any or all of prior embodiments in this paragraph up through the second embodiment in this paragraph further comprising a para-xylene separation unit in downstream communication with the product section of the dividing wall naphthene splitter column via the naphthene splitter sidedraw line. An embodiment of the invention is one, any or all of prior embodiments in this paragraph up through the second embodiment in this paragraph, wherein the para-xylene separation unit being a simulated moving bed adsorption unit using toluene as a desorbent. An embodiment of the invention is one, any or all of prior embodiments in this paragraph up through the second embodiment in this paragraph, wherein the extractive distillation column in is downstream communication with the naphthene splitter overhead line from the product section of the dividing wall naphthene splitter column. An embodiment of the invention is one, any or all of prior embodiments in this paragraph up through the second embodiment in this paragraph further comprising an aromatics rerun column in downstream communication with a naphthene splitter bottoms line from the product s of the dividing wall naphthene splitter column.

A third embodiment of the invention is a process for the production of para-xylene, wherein the process comprises a) introducing a raffinate product stream comprising $C_8$ aromatic isomers to an isomerization unit to provide an isomerized stream, wherein the isomerized stream is produced in the presence of an ethylbenzene (EB) isomerization catalyst; b) passing the isomerized stream to an isomerate stripper column to provide an isomerate stripper overhead stream comprising $C_{6-}$ hydrocarbons and an isomerate stripper bottoms stream; c) passing the isomerate stripper bottoms stream to a dividing wall naphthene splitter column to provide a naphthene splitter sidedraw stream comprising $C_8$ aromatic isomers and less than about 1 wt % of $C_{9+}$ alkylaromatic hydrocarbons; d) passing the overhead naphthene splitter stream to an extractive distillation column to provide a recycle feedstream comprising the $C_8$ naphthenes and an extract stream comprising the $C_7$ aromatic hydrocarbons; and e) passing the recycle feedstream to the isomerization unit. An embodiment of the invention is one, any or all of prior embodiments in this paragraph up through the third embodiment in this paragraph, wherein the naphthene splitter sidedraw stream comprises less than about 0.7 wt % of $C_{9+}$ alkylaromatic hydrocarbons. An embodiment of the invention is one, any or all of prior embodiments in this paragraph up through the third embodiment in this paragraph, wherein the dividing wall naphthene splitter column comprises a dividing wall having an upper end and a lower end that divides the naphthene splitter column into a feed section and a product section. An embodiment of the invention is one, any or all of prior embodiments in this paragraph up through the third embodiment in this paragraph, wherein the dividing wall naphthene splitter column comprises one or more vapor-liquid contacting stages. An embodiment of the invention is one, any or all of prior embodiments in this paragraph up through the third embodiment in this paragraph, wherein the lower end of the dividing wall extends to a last stage of the one or more vapor-liquid contacting stages.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. An apparatus for producing para-xylene, wherein the apparatus comprises:
   a) an isomerization unit to provide an isomerized stream;
   b) an isomerate stripper column in communication with the isomerization unit to provide an isomerate stripper overhead stream comprising $C_{6-}$ hydrocarbons in an isomerate overhead line and an isomerate stripper bottoms stream in an isomerate bottoms line;

c) a dividing wall naphthene splitter column in communication with the isomerate bottoms line to provide an overhead naphthene splitter stream comprising the $C_8$ naphthenes and $C_7$ aromatic hydrocarbons in a naphthene splitter overhead line and a naphthene splitter sidedraw stream comprising $C_8$ aromatic isomers in a naphthene splitter sidedraw line; and d) an extractive distillation column in communication with the naphthene splitter overhead line to provide a recycle feedstream comprising the $C_8$ naphthenes in a recycle line and an extract stream comprising the $C_7$ aromatic hydrocarbons in an extract line.

2. The apparatus of claim 1, wherein the dividing wall naphthene splitter column comprises a dividing wall having an upper end and a lower end that divides the naphthene splitter column into a feed section and a product section.

3. The apparatus of claim 2, wherein the dividing wall naphthene splitter column comprises one or more vapor-liquid contacting stages.

4. The apparatus of claim 3, wherein the lower end of the dividing wall extends to a last stage of the one or more vapor-liquid contacting stages.

5. The apparatus of claim 2, wherein the feed section of the dividing wall naphthene splitter column is in downstream communication with the isomerate bottoms line.

6. The apparatus of claim 1 further comprising a para-xylene separation unit in downstream communication with the product section of the dividing wall naphthene splitter column via the naphthene splitter sidedraw line.

7. The apparatus of claim 6, wherein the para-xylene separation unit being a simulated moving bed adsorption unit using toluene as a desorbent.

8. The apparatus of claim 1, wherein the extractive distillation column in is downstream communication with the naphthene splitter overhead line from the product section of the dividing wall naphthene splitter column.

9. The apparatus of claim 1 further comprising an aromatics rerun column in downstream communication with a naphthene splitter bottoms line from the product section of the dividing wall naphthene splitter column.

10. An apparatus for producing para-xylene, wherein the apparatus comprises:
   a) an isomerization unit to provide an isomerized stream;
   b) an isomerate stripper column in communication with the isomerization unit to provide an isomerate stripper overhead stream comprising $C_{6-}$ hydrocarbons in an isomerate overhead line and an isomerate stripper bottoms stream in an isomerate bottoms line;
   c) a dividing wall naphthene splitter column having one or more vapor-liquid contacting stages comprising a dividing wall having an upper end and a lower end that divides the naphthene splitter column into a feed section and a product section and the lower end of the dividing wall extends to a last stage of the one or more vapor-liquid contacting stages, the dividing wall naphthene splitter being in communication with the isomerate bottoms line to provide an overhead naphthene splitter stream comprising the $C_8$ naphthenes and $C_7$ aromatic hydrocarbons in a naphthene splitter overhead line and a naphthene splitter sidedraw stream comprising $C_8$ aromatic isomers in a naphthene splitter sidedraw line; and
   d) an extractive distillation column in communication with the naphthene splitter overhead line to provide a recycle feedstream comprising the C8 naphthenes in a recycle line and an extract stream comprising the C7 aromatic hydrocarbons in an extract line.

11. The apparatus of claim 10, wherein the feed section of the dividing wall naphthene splitter column is in communication with the isomerate bottoms line.

12. The apparatus of claim 10 further comprising a para-xylene separation unit in downstream communication with the product section of the dividing wall naphthene splitter column via the naphthene splitter sidedraw line.

13. The apparatus of claim 12, wherein the para-xylene separation unit being a simulated moving bed adsorption unit using toluene as a desorbent.

14. The apparatus of claim 10, wherein the extractive distillation column in is downstream communication with the naphthene splitter overhead line from the product section of the dividing wall naphthene splitter column.

15. The apparatus of claim 10 further comprising an aromatics rerun column in downstream communication with a naphthene splitter bottoms line from the product s of the dividing wall naphthene splitter column.

16. A process for the production of para-xylene, wherein the process comprises:
   a) introducing a raffinate product stream comprising $C_8$ aromatic isomers to an isomerization unit to provide an isomerized stream, wherein the isomerized stream is produced in the presence of an ethylbenzene (EB) isomerization catalyst;
   b) passing the isomerized stream to an isomerate stripper column to provide an isomerate stripper overhead stream comprising $C_{6-}$ hydrocarbons and an isomerate stripper bottoms stream;
   c) passing the isomerate stripper bottoms stream to a dividing wall naphthene splitter column to provide an overhead naphthene splitter stream comprising the $C_8$ naphthenes and $C_7$ aromatic hydrocarbons and a naphthene splitter sidedraw stream comprising $C_8$ aromatic isomers and less than about 1 wt % of $C_{9+}$ alkylaromatic hydrocarbons;
   d) passing the overhead naphthene splitter stream to an extractive distillation column to provide a recycle feedstream comprising the $C_8$ naphthenes and an extract stream comprising the $C_7$ aromatic hydrocarbons; and
   e) passing the recycle feedstream to the isomerization unit.

17. The process of claim 16, wherein the naphthene splitter sidedraw stream comprises less than about 0.7 wt % of $C_{9+}$ alkylaromatic hydrocarbons.

18. The process of claim 16, wherein the dividing wall naphthene splitter column comprises a dividing wall having an upper end and a lower end that divides the naphthene splitter column into a feed section and a product section.

19. The process of claim 18, wherein the dividing wall naphthene splitter column comprises one or more vapor-liquid contacting stages.

20. The process of claim 19, wherein the lower end of the dividing wall extends to a last stage of the one or more vapor-liquid contacting stages.

* * * * *